United States Patent [19]
Coxum

[11] Patent Number: 5,906,605
[45] Date of Patent: *May 25, 1999

[54] TORQUABLE GUIDING CATHETER FOR BASKET DEPLOYMENT AND METHOD

[75] Inventor: Tony Coxum, San Jose, Calif.

[73] Assignee: Cardiac Pathways Corporation, Sunnyvale, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/781,281

[22] Filed: Jan. 10, 1997

[51] Int. Cl.$^6$ .................................................. A61M 25/00
[52] U.S. Cl. ........................ 604/525; 604/527; 604/529; 600/373; 600/374; 607/122
[58] Field of Search ..................................... 607/119, 122; 600/373, 374, 377, 381, 585; 604/280, 282

[56] References Cited

U.S. PATENT DOCUMENTS 5,465,717  11/1995  Imran et al. ............................. 607/122
5,487,757  1/1996   Truckai et al. .......................... 607/122
5,531,721  7/1996   Pepin et al. ............................. 604/282
5,702,373  12/1997  Samson ................................... 604/282

Primary Examiner—Jeffrey R. Jastrzab
Assistant Examiner—David M. Ruddy
Attorney, Agent, or Firm—Flehr Hohbach Test Albritton & Herbert LLP

[57] ABSTRACT

A torquable guiding catheter for use in mapping the wall of a heart of the patient with a mapping catheter having a distal extremity and a mapping device carried by the distal extremity and carrying a plurality of electrodes for engaging the wall of the heart. The basket-like device is movable between expanded and contracted positions and in a contracted position having an outside diameter no greater than a predetermined diameter. The torquable guiding catheter comprises a flexible elongate braided shaft assembly having proximal and distal extremities and having a smooth outer surface and also having a smooth inner surface defining a lumen extending from the proximal extremity to the distal extremity. The flexible elongate braided shaft assembly includes a braid formed of flat metal ribbon extending from the proximal extremity to the distal extremity and having plastic covering the braid having a Shore hardness durometer ranging from 55D to 75D. The surface defining the lumen is formed by a liner of a lubricious material adhered to the plastic encapsulating the braid and has a diameter at least as great as the predetermined diameter of the mapping device in a contracted position.

10 Claims, 1 Drawing Sheet

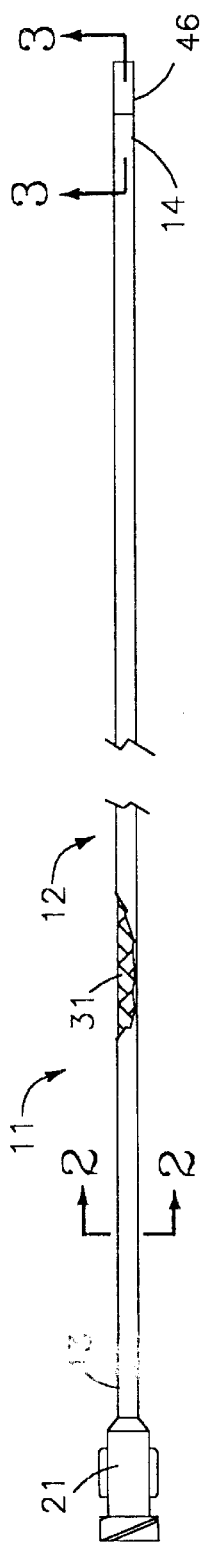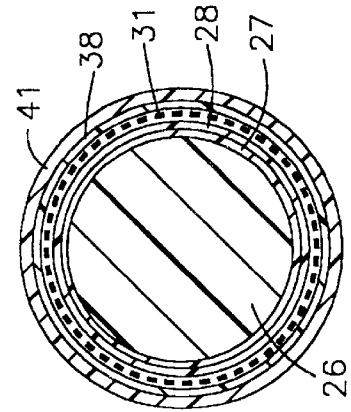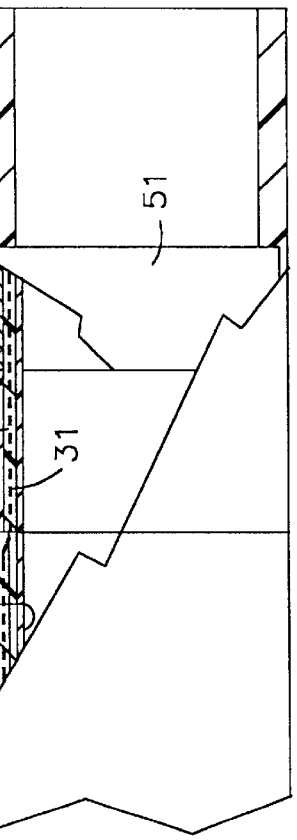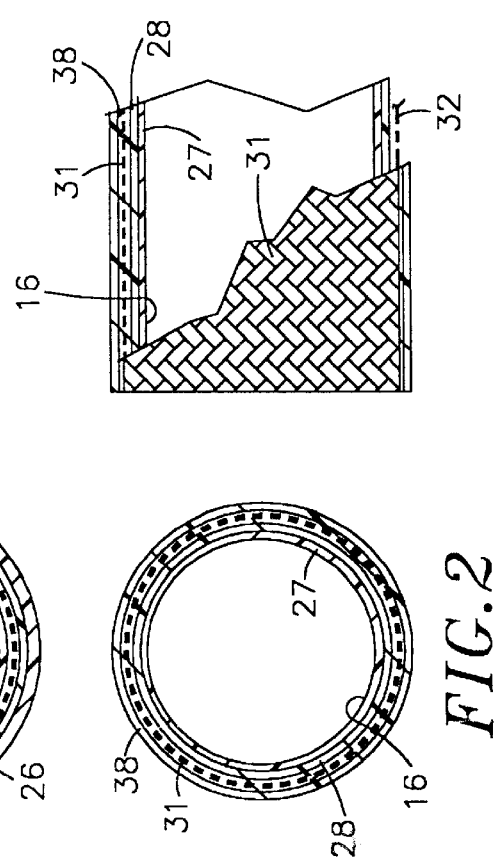

TORQUABLE GUIDING CATHETER FOR BASKET DEPLOYMENT AND METHOD

This application relates to a torquable guiding catheter for use in deploying a mapping catheter having a basket mounted on the distal extremity and a method for manufacture of the torquable guiding catheter.

Heretofore torquable guiding catheters have been provided. However, such torquable guiding catheters have not met the needs for deployment of a mapping catheter having a basket on the distal extremity thereof because they have not been large enough. In addition such torquable guiding catheters have had insufficient kink resistance and have not had the desired pushability. There is therefore a need for a new and improved torquable guiding catheter and a method for manufacture of the same.

In general it is an object of the present invention to provide a torquable guiding catheter which can be utilized for deploying mapping catheters having baskets on the distal extremities thereof and a method for the manufacture of the torquable guiding catheter.

Another object of the invention is to provide a torquable guiding catheter of the above character which has an outside diameter of 11-French and larger and which has a large lumen of 9-French and larger and which has a length sufficient to reach the apex of the heart.

Another object of the invention is to provide a torquable guiding catheter of the above character which has improved kink resistance.

Another object of the invention is to provide a torquable guiding catheter which has improved pushability.

Additional objects and features of the invention will appear from the following description in which the preferred embodiments are set forth in detail in conjunction with the accompanying drawing.

FIG. 1 is a side elevational view of a torquable guiding catheter incorporating the present invention.

FIG. 2 is a cross-sectional view taken along the line 2—2 of FIG. 1.

FIG. 3 is a sectional view taken along the line 3—3 of FIG. 1.

FIG. 4 is a cross-sectional view similar to FIG. 2 showing the manner in which the torquable guiding catheter is manufactured.

The torquable guiding catheter of the present invention is for use in mapping the wall of a heart of a patient with a mapping catheter having a distal extremity and having a basket-like device carried by the distal extremity and carrying a plurality of electrodes for engaging the wall of the heart with the basket-like device being movable between the expanded and contracted positions and in the contracted position having an outside diameter when collapsed of less than 0.118". The torquable guiding catheter is comprised of a flexible elongate member having an outside diameter of approximately 0.144" and having a bore therein defined by an inner surface of the flexible elongate member. The bore extends from the proximal extremity to the distal extremity. A liner of a lubricious material adheres to the inner surface of the bore and defines a flow lumen having a diameter at least as great as 0.115". A braid formed of a flat metal ribbon extends from the proximal extremity to the distal extremity of the flexible elongate member and is secured to the outer surface of the flexible elongate member. An outer jacket of a plastic material is provided which overlies the braid and extends from the proximal extremity to the distal extremity of the flexible elongate member.

More in particular, the torquable guiding catheter 11 as shown in FIGS. 1, 2 and 3 consists of a flexible elongate braided shaft assembly 12 which is provided with proximal and distal extremities 13 and 14. A lumen 16 extends from the proximal extremity to the distal extremity and opens through the distal extremity 14. The flexible elongate braided shaft assembly 12 can have a suitable length as for example 110 cm±1 cm. It preferably has an outer diameter of 11-French corresponding to 0.144"+0.001" or −0.002". The lumen 16 has a suitable size as for example 9-French corresponding to 0.118"+0.001" or −0.002". A conventional female Luer lock fitting 21 is mounted on the proximal extremity 13 and is of suitable size as for example having an I.D. of 0.160".

The flexible elongate braided shaft assembly 12 is fabricated by a method which can be explained in conjunction with FIG. 4. As shown, an elongate mandrel 26 is utilized which is formed of a suitable material such as PTFE (polytetrafluoroethylene) beading having a suitable diameter such as approximately 0.118" corresponding to the size of the lumen 16 which is desired for the torquable guiding catheter 11. This beading can have a suitable length as for example 50±2". This beading which forms the mandrel 26 is a solid and has a smooth outer surface. A liner 27 is then slipped over the mandrel 26. The liner can be formed of a suitable material such as PTFE and has a wall thickness of approximately 0.002". The outer surface of the liner is etched to improve its surface adhesion capabilities. An inner shaft tubing 28 is slid over the liner 27. This tubing has a suitable inside diameter such as 0.128" and an outside diameter of 0.138" to provide a wall thickness of 0.005". It is formed of a suitable material such as PEBAX a polyether block omide having a Shore hardness durometer in the range of from 55D to 72D and preferably a durometer of approximately 60D. The PEBAX preferably is loaded with $BaSO_4$ from 30% to 50% by weight and preferably 40% by weight. After the inner shaft tubing 28 is in place, the assembly 12, the mandrel 26, the liner 27, and the inner shaft tubing 28 are run through a hot die to neck down the assembly so that the inner shaft tubing 28 is bonded to the PTFE liner 27. The hot die (not shown) can be operated at a suitable temperature ranging from 400°–425° F. and preferably about 420° F. and various components can be pulled through the die in unison at a suitable speed ranging from 1–3 feet per minute and preferably about 2 feet per minute.

A braid 31 is then formed over the inner shaft tubing 28 after the assembly is cooled. The braid 31 is formed of a flat metal ribbon or wire having a suitable size, as for example a thickness of 0.002" and a width of 0.007", and is formed of a suitable metal such as stainless steel 304 having a tensile strength of approximately 321 kpsi. The flat wire or ribbon strands 32 are formed into an overlapping braid pattern of the type shown in FIG. 3 with 45 picks per inch. The 45 picks per inch selected for the braid 31 makes it possible to bond the top layer of the tubing to the bottom layer of the tubing between small cracks in the braid pattern permitting plastic to flow between the same during the laminating step to provide additional torsion capabilities for the braid in the torquable guiding catheter. In addition, the flat ribbon braid makes it possible to torque the torquable guiding catheter without whipping. That is, there is a substantial one to one correspondence between torquing of the proximal extremity of the catheter and movement of the distal extremity of the catheter.

After the braid 31 has been formed on the shaft tubing 28, an outer shaft tubing 38 formed of the same material as inner shaft tubing 28, but preferably of a different durometer and preferably of a higher durometer, is slid over the outside of the braid 31 and extends over the entire length of the mandrel 26. Thereafter, a shrink tube 41 formed of a suitable material such as FEP (fluorinated ethylene polyprophylene) is slid over the outer shaft tubing 38 to enclose the same. This assembly with the shrink tubing thereon is then passed through a hot die at a suitable temperature ranging from 500° F. to 550° F. and preferably about 520° F. at a speed ranging from 1–3 feet per minute and preferably about 2 feet per minute to cause the shrink tubing to compress the entire assembly and to permit sufficient heat to be applied to the assembly so that the liner 27, the inner shaft tubing 28, the braid 31 and the outer shaft tubing 38 are laminated together without the shrink tubing becoming a part of the laminated assembly. This is true because the FEP material utilized for the shrink tube can take the heat required for the lamination of the other layers of the assembly without itself melting and becoming part of the laminate.

After the assembly shown in FIG. 4 has been cooled to near room temperature, the shrink tube 41 can be cut and peeled off so that the outer shaft tubing 38 form an outer jacket which has a very smooth surface corresponding to the smooth inner surface of the FEP shrink tubing 41.

It should be appreciated it is feasible in production to eliminate the use of the shrink tubing and to laminate the assembly shown in FIGS. 3 and 4 without the use of a shrink tube and thereafter grinding the outer surface of the outer shaft tubing 38 to provide the desired smoother surface.

After the shrink tubing 41 has been peeled off, the ends can be trimmed after which the mandrel 26 can be removed. This can be readily accomplished because the TFE beading which forms the mandrel 26 elongates and reduces in diameter when pulled, facilitating its removal from the liner 27. It should be appreciated that although removal of a mandrel of other materials may be more difficult they still can be utilized. For example, copper coated stainless steel can be utilized for a mandrel.

A soft atraumatic tip 46 is provided which forms the distal extremity of the flexible elongate braided shaft assembly. This tip 46 is formed by taking the mandrel 26 or a small piece thereof and inserting it into the lumen 16 at one end as for example the distal extremity. A capture tube (not shown) formed of a suitable material, as for example a low durometer Pebax as hereinbefore described is extended over the outer surface of the outer shaft tubing 38 from the distalmost extremity for a distance of approximately 5 mm. Heat is then applied to this particular portion of the capture tube to cause the distal extremity to shrink down as shown at 47 in FIG. 3 and to provide an annular edge 48. After this has been accomplished the capture tube is removed by slitting it and peeling it off. A marker band formed of a suitable radiopaque material such as an alloy of 90% platinum and 10% iridium is provided. The band 51 is cylindrical in shape and has a suitable length as for example 0.060" and an inside diameter of 0.1360" and a suitable wall thickness as for example 0.002". This marker band 51 is slid over the portion 47 of reduced diameter so that it is approximately 2 mm distal of the edge 48 and is secured by an adhesive to the portion 47 so that it has its distalmost portion in general alignment with the distalmost portion of the heat shrunk portion 47 as shown in FIG. 3. A length of PEBAX tubing 52 is then provided having a suitable length as for example 26 mm is slid over the portion 47 and over the marker band 51. The PEBAX tubing 52 is softer than the PEBAX tubing hereinbefore utilized for the inner shaft tubing 28 and the outer shaft tubing 38 and for example can have a Shore hardness durometer ranging from 25D to 40D and preferably approximately 35D.

After the tubing 52 is in place, a piece of FEP shrink tubing of the type hereinbefore described (not shown) is placed over the tubing 52 and is heated to cause at least a partial melting of the tubing 52 to cause lamination of the tubing 52 to the portion 47 and to encapsulate the marker band 51. This causes the outer surface of the tubing 52 to be flush with the outer surface of the outer shaft tubing 38. After the tubing 52 has cooled, the shrink tubing can be slit and peeled off after which the mandrel can be removed. The distal extremity can then be trimmed to provide the flush atraumatic tip which is shown in FIGS. 1 and 3.

The fitting 21 hereinbefore described can then be affixed to the other end of the flexible elongate braided shaft assembly 12 by boring a hole of appropriate size in the fitting to accommodate the proximal extremity of the assembly 12. The fitting then can be bonded to the proximal extremity in a suitable manner as for example utilizing conventional adhesive which can be cured by ultraviolet. This completes the manufacture of the device 11 shown in FIG. 1 which has a straight distal extremity.

If desired, it is possible to provide a torquable guiding catheter 11 which has an angle in the distal extremity as for example a 30° angle. The placement of an angle in the distal extremity of a catheter can be readily accomplished. For example a mandrel 26 formed of the beading hereinbefore described can be positioned in the distal extremity. The distal extremity with the mandrel therein can then be placed in a grooved template as for example first and second plates (not shown) which have grooving therein corresponding to the desired bend as for example a 30° bend. The entire assembly is then heated to a suitable temperature, as for example 280–300° F. for a period of time ranging from 1–5 minutes. After sufficient heat has been applied, the distal extremity is removed from the hot plate and quenched in a suitable manner as for example quenching it in tap water to provide a permanent 30° set in the distal extremity. Other angles can be formed in a distal extremity of a torquable guiding catheter 11 in a similar manner.

Operation and use of the torquable guiding catheter 11 in connection with a mapping procedure can be carried out in mapping a chamber of the heart of a human patient. In such a procedure typically, a puncture is made to obtain access to the femoral artery after which a conventional sheath is inserted. The torquable guiding catheter of the present invention is then introduced into the sheath and into the femoral artery and its distal extremity introduced into, for example, the left ventricle of the heart of the patient. This can be readily accomplished by the physician by pushing on and torquing the proximal extremity of the catheter to cause the distal extremity to advance into the vessel until its distal extremity is in the left ventricle. During the time of introduction of the torquable guiding catheter it is desirable to have the mapping catheter which has a basket-like assembly disposed on its distal extremity positioned within the torquable guiding catheter 11 with its distal extremity within the distal extremity 14 of the torquable guiding catheter. In addition as described in U.S. Pat. No. 5,465,717, a pigtail catheter as well as a guide wire can be utilized to facilitate the appropriate positioning of the distal extremity of the torquable guiding catheter. When a guide wire is used, the guide wire is first inserted after which the pigtail catheter can be advanced utilizing the guide wire. The pigtail catheter can then be utilized for guiding the present torquable guiding catheter 11. More specifically an 8.5 French pigtail catheter can be loaded inside the torquable guiding catheter 11 of 11-French size and introduced into the femoral artery by the use of an 11-French introducer sheath. The pigtail catheter and the torquable guiding catheter 11 are advanced over the aortic arch to the aortic valve. The pigtail catheter is then advanced past the torquable guiding catheter 11 through the aortic valve and into the apex. A torquable guiding catheter 11 is then advanced over the pigtail catheter until it is positioned near the apex. The torquable guiding catheter can be torqued either with the pigtail catheter inside of it or with the pigtail catheter withdrawn in order to direct the tip of the torquable guiding catheter 11 towards the desired location for deployment of the mapping basket. For example if the patient has an apical anterior wall aneurism and the clinician wishes to map the border of the aneurism, the clinician can torque the torquable guiding catheter of the present invention so that the tip faces the anterior wall. The mapping catheter which can be of the type described in U.S. Pat. No. 5,465,717 after removal of the pigtail catheter can be inserted into the torquable guiding catheter. The basket-like device carried by the distal extremity of the basket catheter is movable between expanded and contracted positions and in a contracted position has a maximum diameter of approximately 0.115" so that it can readily slide through the lumen 16 provided by the liner 27. With the basket-like device in contracted or collapsed position it can be readily introduced into the lumen 17 of the torquable guiding catheter 11 and then readily advanced therethrough because of the low friction qualities of the liner 27. As soon as it has reached the desired mapping location, the torquable guiding catheter 11 can be retracted and the basket deployed from the distal extremity thereof and thereafter expanded to cause the electrodes carried thereby to be moved into contact with the wall of the heart to permit the electrodes to pick up the electrical signals at that location and to supply them to the computer apparatus connected to the mapping catheter. It should be appreciated that in order to obtain the desired position for deployment of the basket catheter, either a straight torquable guiding catheter 11 such as shown in FIG. 1 can be utilized or alternatively a guiding catheter having a bend in the distal extremity, as for example a bend of 30° or another angle can be utilized to facilitate such positioning. The torquable guiding catheter 11 of the present invention makes it possible for the clinician or physician to carefully control the placement of the tip so that the basket of the basket catheter when deployed will be in the proper position to perform the desired mapping.

After the desired mapping potentials have been recorded, the basket of the mapping catheter can be contracted by withdrawing it into the torquable guiding catheter 11. The torquable guiding catheter 11 then can be removed along with the basket catheter. It also should be appreciated that if it is desired to deploy the basket of the basket catheter at a different location, the basket can be contracted and brought into the distal extremity of the torquable guiding catheter and then the torquable guiding catheter manipulated to move its distal extremity to another desired location in the chamber of the heart. The basket of the basket catheter can then again be deployed from the distal extremity of the torquable guiding catheter 11 and additional mapping carried out on the wall of the heart. Thus one or more mapping procedures can be carried out in the wall of the heart without withdrawing the torquable guiding catheter 11. from the chamber of the heart in which it is positioned.

It is apparent from the foregoing that there has been provided a torquable guiding catheter which has greatly improved pushability and torquability and which is of a large size so that it can accommodate basket catheters and which can aid in positioning the basket catheters in chambers of the heart so that they are located in the appropriate positions for performing the desired mapping. The torguable guiding catheter is also sized so that it can be used with mapping catheters having various types of mapping devices on the distal extremity. Such mapping devices can have a variety of complex shapes when moved from a contracted condition to an expanded condition, as for example flat coils, flowers and stars. The torquable guiding catheter is provided with a very smooth outer surface. It also has a smooth inner surface to permit the basket of the basket-like device carried by the distal extremity of the basket catheter to be readily advanced through the torquable guiding catheter.

Also, the torquable guiding catheter is sized so that it has a lumen of a size that provides a space between the wall forming the lumen and the outside of the basket catheter that can be used for saline flushing only or for introducing a heparinized saline solution to prevent thrombus formation.

What is claimed is:

1. A torquable guiding catheter for use in mapping the wall of a heart of the patient with a mapping catheter having a distal extremity and a mapping device carried by the distal extremity, the mapping device carrying a plurality of electrodes for engaging the wall of the heart, the mapping device being movable between expanded and contracted positions and in a contracted position having an outside diameter no greater than a predetermined diameter, the torquable guiding catheter comprising a flexible elongate braided tubular shaft assembly having proximal and distal extremities and having a smooth outer surface of constant diameter and a smooth inner surface free of lap joint type bonds extending from said proximal extremely to said distal extremity, said smooth inner surface defining a lumen extending from the proximal extremity to near the distal extremity, the flexible elongate braided shaft assembly including a braid formed of flat metal ribbon extending continuously from the proximal extremity to near the distal extremity and having a continuous plastic covering the braid having a Shore hardness durometer ranging from 55D to 75D to provide a predictable overall torquability and flexibility for the torquable guiding catheter, said inner smooth continuous surface defining the lumen being formed by a liner of a lubricious material adhered to the plastic encapsulating the braid and having a diameter at least as great as the predetermined diameter of the mapping device in a contracted position extending from the proximal extremity to the distal extremity.

2. A torquable guiding catheter as in claim 1 wherein said plastic material encapsulating said braid is formed of a polyether block amide loaded with a radiopaque material.

3. A torquable guiding catheter as in claim 1 wherein said liner is formed of polytetrafluoroethylene.

4. A torquable guiding catheter as in claim 3 wherein said lumen has a predetermined diameter of at least 0.118".

5. A torquable guiding catheter as in claim 1 wherein said outer surface has a diameter of 11-French.

6. A torquable guiding catheter as in claim 1 wherein said flat ribbon has a size ranging from 0.001"×0.002" to 0.002"×0.007".

7. A torquable guiding catheter as in claim 1 wherein the distal extremity includes an atraumatic tip, said atraumatic tip being formed of a material having a durometer substantially less than the durometer of the plastic utilized for the encapsulation of the braid.

8. A torquable guiding catheter as in claim 7 wherein a portion of the flexible elongate tubular braided shaft assembly adjacent said atraumatic tip has braid therein of reduced diameter together with a radiopaque band disposed over the braid of reduced diameter.

9. A torquable guiding catheter for use in mapping the wall of a heart of a patient with a mapping catheter comprising a flexible elongate tubular braided shaft assembly having proximal and distal extremities and including a continuous braid formed of flat metal ribbon extending from the proximal to near the distal extremity, a continuous plastic encapsulating the braid, said flexible elongate tubular braided shaft assembly having an outer surface of a substantially constant diameter free of lap joint type bonds and extending from said proximal extremity to said distal extremity; a layer of lubricious material disposed within the braid and defining a lumen extending from the proximal extremity to the distal extremity of the braided shaft assembly, said braided shaft assembly having a construction to provide a predictable overall torquability for the torquable guiding catheter.

10. A torquable guiding catheter as in claim 9 wherein said plastic encapsulating the braid has a first Shore hardness durometer, and wherein said distal extremity comprises an atraumatic tip, said atraumatic tip being formed of a plastic having a durometer substantially less than the durometer of the plastic encapsulating the braid.

* * * * *